US009851306B2

(12) United States Patent
Laitala

(10) Patent No.: US 9,851,306 B2
(45) Date of Patent: Dec. 26, 2017

(54) REDUCING MEASUREMENT VARIATION RELATED TO OPTICAL MEASURE OF SAMPLE MATERIAL

(75) Inventor: Ville Laitala, Turku (FI)

(73) Assignee: WALLAC OY, Turku (FI)

( * ) Notice: Subject to any disclaimer, the term of this patent is extended or adjusted under 35 U.S.C. 154(b) by 205 days.

(21) Appl. No.: 14/117,991

(22) PCT Filed: Apr. 2, 2012

(86) PCT No.: PCT/FI2012/050330
§ 371 (c)(1),
(2), (4) Date: Jan. 8, 2014

(87) PCT Pub. No.: WO2012/156576
PCT Pub. Date: Nov. 22, 2012

(65) Prior Publication Data
US 2014/0150517 A1    Jun. 5, 2014

Related U.S. Application Data

(60) Provisional application No. 61/487,882, filed on May 19, 2011.

(30) Foreign Application Priority Data

May 19, 2011    (FI) .................................... 20115483

(51) Int. Cl.
*G01N 21/75*    (2006.01)
*G01N 21/64*    (2006.01)
*G01D 18/00*    (2006.01)

(52) U.S. Cl.
CPC ............. *G01N 21/75* (2013.01); *G01D 18/00* (2013.01); *G01N 21/6452* (2013.01)

(58) Field of Classification Search
CPC .............. G01N 21/6452; G01N 21/75; G01N 21/6428–21/645; G01N 21/253; G01D 18/00

(Continued)

(56) References Cited

U.S. PATENT DOCUMENTS 3,879,127 A * 4/1975 Storr ...................... G01N 1/405
 210/656
4,937,637 A * 6/1990 Magistro ............ G01N 21/5907
 356/73

(Continued)

FOREIGN PATENT DOCUMENTS

EP    0 841 557 A2    5/1998
WO    01/23890 A1    4/2001

(Continued)

OTHER PUBLICATIONS

Peters, Statistics for Analysis of Experimental Data, 2001, Published as a chapter in the Environmental Engineering Processes Laboratory Manual S. E. Powers, Ed. AEESP, Champaign, IL 2001.*

(Continued)

*Primary Examiner* — Peter Macchiarolo
*Assistant Examiner* — David L Singer
(74) *Attorney, Agent, or Firm* — Young & Thompson

(57) ABSTRACT

A measurement device includes mechanical support elements (101-104) for supporting a sample well, other mechanical support elements (105-109) for supporting a measurement head (112) suitable for optical measurements, and a control system (111) configured to control the measurement head to carry out at least two optical measurements from at least two different measurement locations inside the sample well, where each measurement location is a center point of a capture range from which radiation is captured in (Continued)

the respective optical measurement. The final measurement result is formed from the results of the at least two optical measurements in accordance with a pre-determined rule. The use of the at least two optical measurements from different measurement locations reduces measurement variation in situations where the sample well (153) contains a piece (158) of sample carrier.

15 Claims, 5 Drawing Sheets

(58) Field of Classification Search
    USPC .......................................................... 73/1.02
    See application file for complete search history.

(56) References Cited

U.S. PATENT DOCUMENTS

| | | | | |
|---|---|---|---|---|
| 5,460,057 | A * | 10/1995 | Ostrup | B01L 3/545 422/65 |
| 6,024,920 | A | 2/2000 | Cunanan | |
| 6,042,785 | A * | 3/2000 | Harju | 422/52 |
| 6,180,409 | B1 * | 1/2001 | Howard, III | G01N 21/8483 422/65 |
| 6,388,788 | B1 | 5/2002 | Harris et al. | |
| 7,199,879 | B2 * | 4/2007 | Harju et al. | 356/417 |
| 8,542,349 | B2 * | 9/2013 | Laitinen et al. | 356/32 |
| 2003/0203490 | A1 | 10/2003 | Vuong | |
| 2004/0257590 | A1 * | 12/2004 | Hummel | G01N 21/6452 356/630 |
| 2006/0269450 | A1 * | 11/2006 | Kim | G01N 21/6452 422/82.05 |
| 2010/0182419 | A1 | 7/2010 | Jiang | |
| 2011/0033872 | A1 * | 2/2011 | Vaisanen | G01N 21/15 435/7.1 |
| 2011/0034343 | A1 * | 2/2011 | Erling | B01L 3/5085 506/7 |
| 2012/0104280 | A1 * | 5/2012 | Manian | 250/459.1 |

FOREIGN PATENT DOCUMENTS

| | | |
|---|---|---|
| WO | 2009130378 A1 | 10/2009 |
| WO | 2010/037907 A1 | 4/2010 |
| WO | 2010/084244 A1 | 7/2010 |

OTHER PUBLICATIONS

Osborne et al, The power of outliers (and why researchers should always check for them), 2004, Practical Assessment, Research & Evaluation.*
French Search Report, dated Jan. 18, 2012, from corresponding French application.
International Search Report, dated Jul. 10, 2012, from corresponding PCT application.

* cited by examiner

REDUCING MEASUREMENT VARIATION RELATED TO OPTICAL MEASURE OF SAMPLE MATERIAL

FIELD OF THE INVENTION

The invention relates to a method for reducing measurement variation related to optical measuring of sample material in situations where a sample well contains the sample material and a piece of sample carrier. Furthermore, the invention relates to a measurement device and to a computer program for reducing measurement variation related to optical measuring of sample material.

BACKGROUND

A widely used practice in chemical analysis is to impregnate one or more drops of liquid sample material to be examined onto a sample carrier, dry the sample carrier impregnated with the sample material, and then send the sample carrier to a laboratory for examination. The sample material to be examined can be, for example, blood and the sample carrier can be, for example, a sheet of filter paper or some other suitable material which is able to absorb the sample material. In the laboratory, one or more pieces containing the sample material to be examined are cut or punched out from the sample carrier and the piece that has been cut off is conveyed to a sample well of e.g. a micro-titration plate for further analysis. The further analysis typically comprises eluting the sample material or at least part of it into sample solution in the sample well, carrying out a chemical or biochemical reaction, and subsequently carrying out an optical measurement from the sample well. The desired chemical reaction can also occur directly on the surface of the sample carrier, and the elution of the sample material is in this case not necessary.

The optical measurement can be, for example, a fluorescence measurement, a time gated fluorescence intensity measurement, a fluorescence life-time measurement, a luminescence measurement, or an absorbance measurement. The piece of the sample carrier places itself stochastically in the sample well. The stochastic location of the piece of the sample carrier in the sample well with respect to the location of the capture range of the optical measurement may influence the optical measurement result because the piece of the sample carrier may attenuate or enhance the radiation being measured. In conjunction with certain analysis methods, the piece of the sample carrier can be dark because of coloring substances, e.g. hemoglobin, which can be on the surface of the piece. In this case, the piece may disturb the optical measurement by attenuating the measured radiation even if the piece were on the bottom of the sample well. However, also in cases where the piece is white, the piece can disturb the optical measurement by typically enhancing the measured radiation.

An inconvenience related to the above described phenomenon is that it may increase the measurement deviation between replicated samples and thus it may cause additional work and additional requirements to personnel performing the optical measurements in laboratories. An optical measurement according to the prior art has to be usually taken from such a sample well that does not contain the piece of the sample carrier, i.e. the piece has been removed from the sample well or the substance to be measured has been transferred to another sample well prior to the measurement.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the first aspect of the invention, there is provided a new method for reducing measurement variation related to optical measuring of sample material. The method according to the invention comprises:

carrying out at least two optical measurements from at least two different measurement locations inside a sample well that contains the sample material and a piece of sample carrier, each measurement location being a center point of a capture range from which radiation is captured in the respective optical measurement, and subsequently forming a final measurement result from the results of the at least two optical measurements in accordance with a pre-determined rule.

As the two or more optical measurements are taken from different measurement locations inside the sample well, the disturbing effect of the stochastic location of the piece of the sample carrier is reduced. Thus there is no need to remove the piece of the sample carrier from the sample well and nor there is a need to transfer the substance to be measured to another sample well prior to the measurements. The above-mentioned piece of sample carrier is, preferably but not necessarily, material, e.g. paper, capable of absorbing the sample material. In principle, the piece of sample carrier could also be a piece of plastic film onto surface of which e.g. blood has been dried.

In cases where only two optical measurements are carried out, the measurement locations are advantageously situated on opposite fringes of the interior of the sample well. In cases where more than two optical measurements are carried out, the measurement locations can be situated, for example, so that one of them is substantially on the middle of the sample well and the other measurement locations are substantially symmetrically around it. The final measurement result can be, for example, the maximum, the minimum, or the arithmetic mean of the results of the at least two optical measurements.

In accordance with the second aspect of the invention, there is provided a new measurement device comprising:

first mechanical support elements for supporting a sample well, second mechanical support elements for supporting a measurement head that is suitable for optical measurements, and a control system for controlling operation of the measurement head.

The control system is configured to control the measurement head to carry out at least two optical measurements from at least two different measurement locations inside the sample well, each measurement location being a center point of a capture range from which radiation is captured by the measurement head in the respective optical measurement. The control system is further configured to form a final measurement result from the results of the at least two optical measurements in accordance with a pre-determined rule.

It should be noted that the above-described measurement device does not necessarily comprise the measurement head because the measurement head can be an external, replaceable component that can be detachably attached to the second mechanical support elements. Correspondingly, the measurement device does not typically comprise the sample well but the first mechanical support elements may comprise, for example, a movable sledge element suitable for receiving a sample plate that comprises many sample wells.

The operation where the at least two optical measurements are taken from different measurement locations inside the sample well can be accomplished in many ways. The control system can be configured to control the first mechanical support elements to move the sample well in at least one dimension in the plane of the opening of the sample well when changing from one of the measurement locations to another of the measurement locations. Alternatively, the control system can be configured to control the second mechanical support elements to move the measurement head in at least one dimension in the plane of the opening of the sample well when changing from one of the measurement locations to another of the measurement locations. It is also possible that the measurement head comprises two or more optical input interfaces which can capture radiation from different measurement locations from the sample well without a need to change the mutual position of the measurement head and the sample well.

In accordance with the third aspect of the invention, there is provided a new optical measurement instrument comprising:
    a measurement device according to the invention, and
    a measurement head attached to the second mechanical support elements of the measurement device.

Hence, in this document the term "optical measurement instrument" is used for a measurement device which has been equipped with a measurement head, wherein the measurement head can be either an integral or replaceable component of the optical measurement instrument. The measurement head may comprise, for example, optical elements for capturing the radiation from the sample well and for directing the captured radiation to a detector that is configured to convert the captured radiation into an electrical signal. The optical elements may contain for example lenses, fibers, mirrors, dichroic mirrors, optical filters, monochromators, and/or other optical elements. The detector can be, for example, a photodiode or a photomultiplier tube.

In accordance with the fourth aspect of the invention, there is provided a new computer program for the purpose of reducing measurement variation related to optical measuring of sample material. The computer program comprises computer executable instructions for controlling a programmable processor to:
    control a measurement head of an optical measurement instrument to carry out at least two optical measurements from at least two different measurement locations inside a sample well containing at least the sample material and a piece of sample carrier, each measurement location being a center point of a capture range from which radiation is captured in the respective optical measurement, and
    form a measurement result from results of the at least two optical measurements in accordance with a pre-determined rule.

The computer program may further comprise computer executable instructions for controlling the programmable processor to form a final measurement result from results of the at least two optical measurements in accordance with a pre-determined rule.

A computer program product according to the invention comprises a non-volatile computer readable medium, e.g. a compact disc ("CD"), encoded with a computer program according to the invention.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EXEMPLIFYING EMBODIMENTS

Figure 1A:
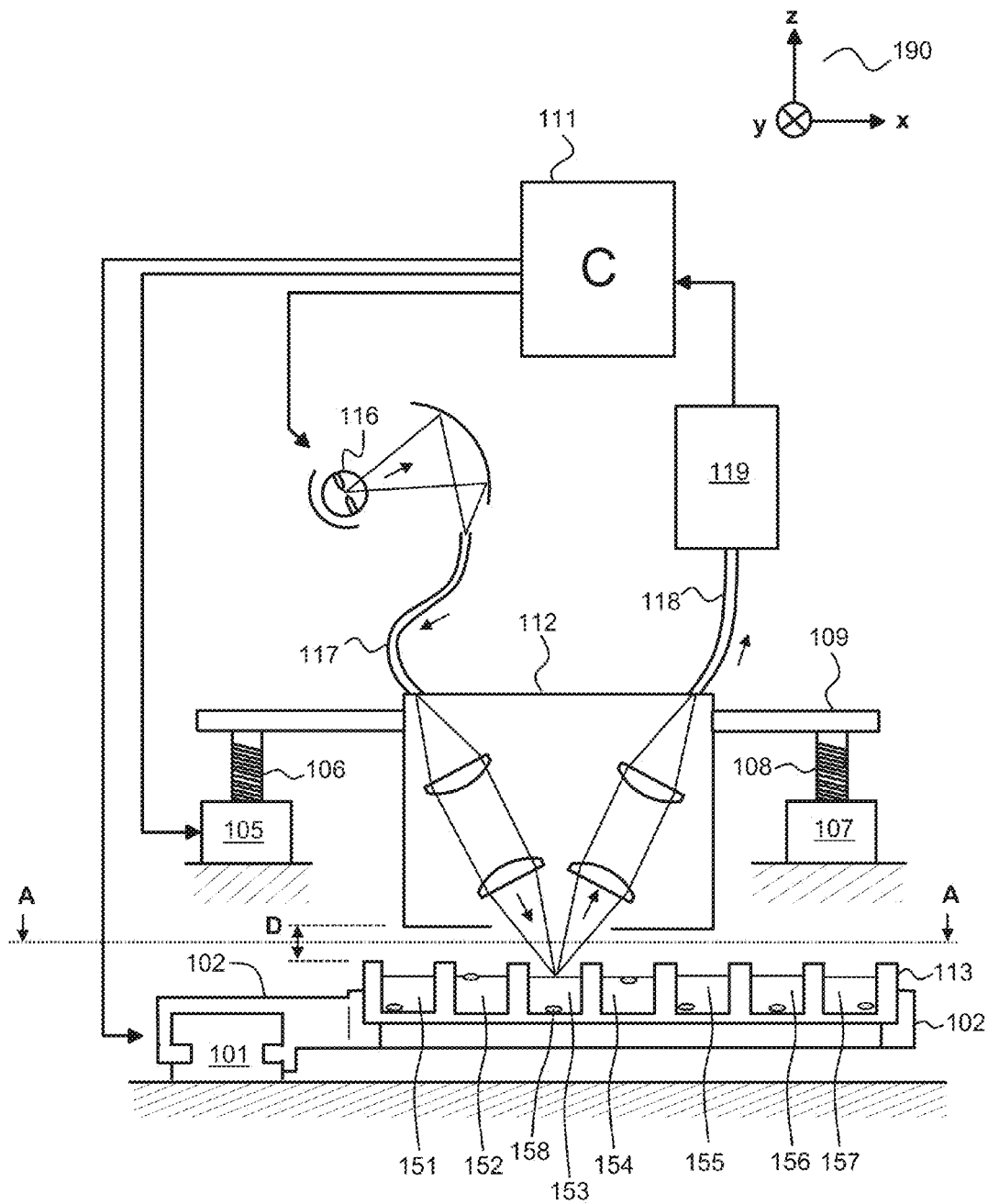
FIG. 1a shows a schematic illustration of an optical measurement instrument according to an embodiment of the invention.
Figure 1B:
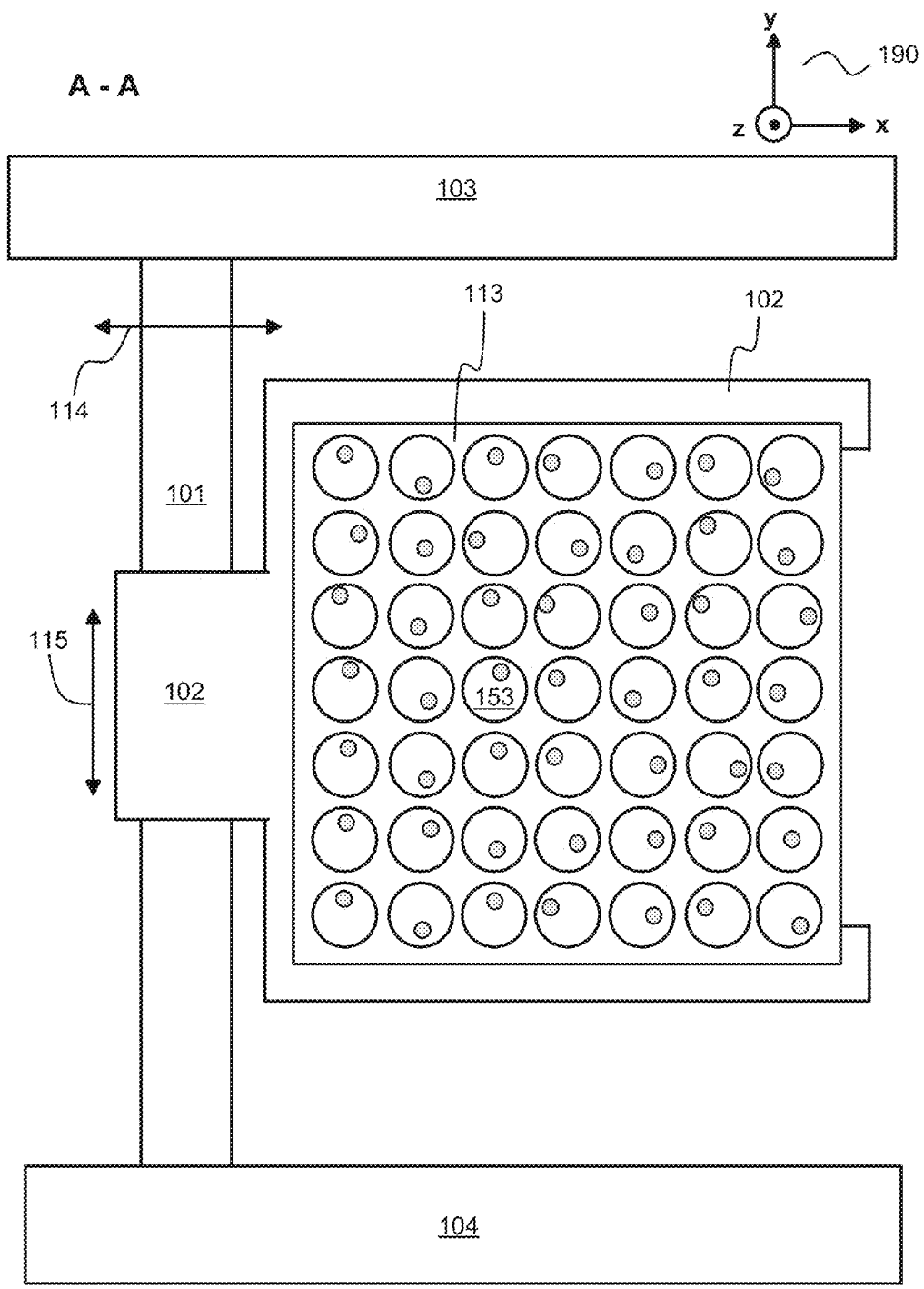
FIG. 1b shows a schematic illustration of a view seen downwards from line A-A of FIG. 1a, FIGS. 1c, 1d, and 1e show schematic illustrations of arrangements of capture ranges related to optical measurements taken from a sample well.

FIG. 1a shows a schematic illustration of an optical measurement instrument according to an exemplifying embodiment of the invention. FIG. 1b shows schematic illustration of a view seen downwards from line A-A of FIG. 1a. The optical measurement instrument comprises first mechanical support elements arranged to support a sample plate 113 that can be e.g. a microtitration plate. The sample plate comprises sample wells 151, 152, 153, 154, 155, 156, and 157. In this example, the sample wells are circular when seen from top but the sample wells could as well be e.g. rectangular. In the exemplifying situation shown in FIGS. 1a and 1b, each of the sample wells contains measurement solution and a piece of sample carrier from which at least part of sample material has eluted in the measurement solution. It should be noted that the desired chemical reaction can also occur directly on the surface of the sample carrier, and the elution of the sample material is not necessary. In this case, an optical measurement has to be taken directly from the piece of the sample carrier. In the exemplifying situation shown in FIGS. 1a and 1b, the sample well 153 contains the piece 158 of the sample carrier. The sample material can be, for example, blood and the sample carrier can be, for example, a sheet of filter paper or some other suitable material which is able to absorb the sample material. The first mechanical support elements comprise a support rail 101 and guide elements 103 and 104 shown in FIG. 1b. The support rail 101 is supported relative to a body of the optical measurement instrument with the aid of the guide elements 103 and 104 in such a way that the support rail is movable in the directions of a two-headed arrow 114 shown in FIG. 1b. The first mechanical support elements comprise a sledge 102 capable of receiving the sample plate 113. The sledge is connected to the support rail 101 in such a way that the sledge is capable of sliding along the support rail in the longitudinal direction of the support rail, i.e. the sledge is movable in the directions of a two-headed arrow 115 shown in FIG. 1b. Hence, the sample wells of the sample plate 113 are movable in the xy-plane defined by a co-ordinate system 190. Due to the fact that the sample wells are movable in the xy-plane, the contents of different sample wells can be measured in a temporally successive manner so that each sample well is in turn the sample well whose content is being measured.

The optical measurement instrument comprises an excitation light source 116 that can be for example a flash lamp such as a xenon flash lamp. The excitation light produced by the excitation light source is focused with a concave mirror to a light guide 117 that can be e.g. a fiber bundle. The light guide 117 is connected to a measurement head 112 that comprises two channels, one for the excitation radiation and another for an emission radiation emitted by the sample material contained by the sample well 153. In the exemplifying case illustrated in FIG. 1a, the measurement head 112 comprises plano-convex lenses arranged to focus the excitation radiation to the sample material being measured and to collect the emission radiation from the sample material. It is also possible that the measurement head comprises an arrangement for exciting and measuring the sample material via a same lens so that there is a dichroic mirror which reflects excitation wavelength but allows the emission wavelength to go through the mirror. The emission radiation is conducted via a light guide 118 to a detector 119 arranged to detect the emission radiation emitted by the sample material and to produce a detection signal responsive to the detected emission radiation. The detector can be for example a photodiode or a photomultiplier tube. The measurement head 112, the excitation light source 116, the detector 119, and/or the light guides 117 and 119 can be either integral or replaceable components of the optical measurement instrument.

The optical measurement instrument comprises second mechanical support elements arranged to support the measurement head 112. In the exemplifying case illustrated in FIGS. 1a and 1b, the second mechanical support elements comprise threaded rods 106 and 108, counterparts 105 and 107 of the threaded rods, and a planar element 109 having an aperture for the measurement head 112.

The counterparts 105 and 107 of the threaded rods may comprise, for example, servomotors arranged to move the measurement head 112 in the positive or negative z-direction of the co-ordinate system 190. Thus, in the exemplifying case illustrated in FIGS. 1a and 1b, the second mechanical support elements allow the vertical distance D from the measurement head 112 to the sample plate 113 to be changed.

The optical measurement instrument comprises a control system 111 for controlling the operation of the measurement head 112. The control system is configured to control the measurement head and the first mechanical support elements 101-104 so that at least two optical measurements are taken from at least two different measurement locations inside the sample well 153. The control system 111 is configured to control the first mechanical support elements to move the sample well 153 in the xy-plane relative to the body of the optical measurement instrument in order to change from one of the measurement locations to another of the measurement locations, where each measurement location is a center point of a capture range from which radiation is captured in the respective optical measurement. The sample well 153 is advantageously moved in the xy-plane in a so cautious way that the piece 158 of the sample carrier does not substantially move with respect to the sample well. This can be achieved, for example, by configuring appropriate acceleration limits, and possibly also speed limits, for servomotors arranged to move the sample well. The acceleration limits can be implemented with limiter devices arranged to limit the electrical current of the servomotors and the speed limit can be implemented with a limiter device arranged to limit the voltage or supply frequency depending on the type of the servomotors. The control system 111 is configured to form a final measurement result from the results of the at least two optical measurements in accordance with a pre-determined rule. The use of the two or more optical measurements from the different measurement locations reduces the disturbing effect of the stochastic location of the piece 158 of the sample carrier in the sample well 153. The final measurement result can be, for example, the maximum, the minimum, or the arithmetic mean of the results of the at least two optical measurements. In practice, it has turned out to be appropriate that optical measurements are taken from five measurement locations inside the sample well and the final result is a weighted or non-weighted average of two or three greatest, or smallest, of the five results of the optical measurements.

In an optical measurement instrument according to an exemplifying embodiment of the invention, the capture range of each optical measurement is an ellipsoid. The ellipsoid is typically formed when a xenon flash lamp is used for generating excitation light whereas, when using a laser, more point-form excitation can be achieved and thus also the capture range of each optical measurement can be more point-form. The embodiments of the present invention are naturally also applicable in conjunction with the laser excitation. The control system 111 is configured to control the mutual positions of the sample well 153 and the measurement head 112 so that the capture ranges of two optical measurements are situated on opposite fringes of the interior of the sample well so that the secondary, i.e. the shortest, axes of the ellipsoids representing these capture ranges coincide substantially with a same diameter line 192 of the sample well. A case of the kind described above is illustrated in FIG. 1c which shows a schematic illustration of the sample well 153 seen downwards from the line A-A of FIG. 1a. Ellipsoids 161 and 162 drawn with dashed lines represent the capture ranges of the optical measurements to be taken from the sample well. The piece 158 of the sample carrier is depicted with a gray circle. As can be seen form FIG. 1c, at least one of the capture ranges is not even partially shadowed by the piece of the sample carrier. The final measurement result is advantageously the maximum of the results of the two optical measurements. It also is possible to have more than two, e.g. five, ellipsoids representing the capture ranges so that the secondary axes of the ellipsoids representing these capture ranges coincide substantially with the same diameter line of the sample well, see FIG. 1e.

Figure 4:
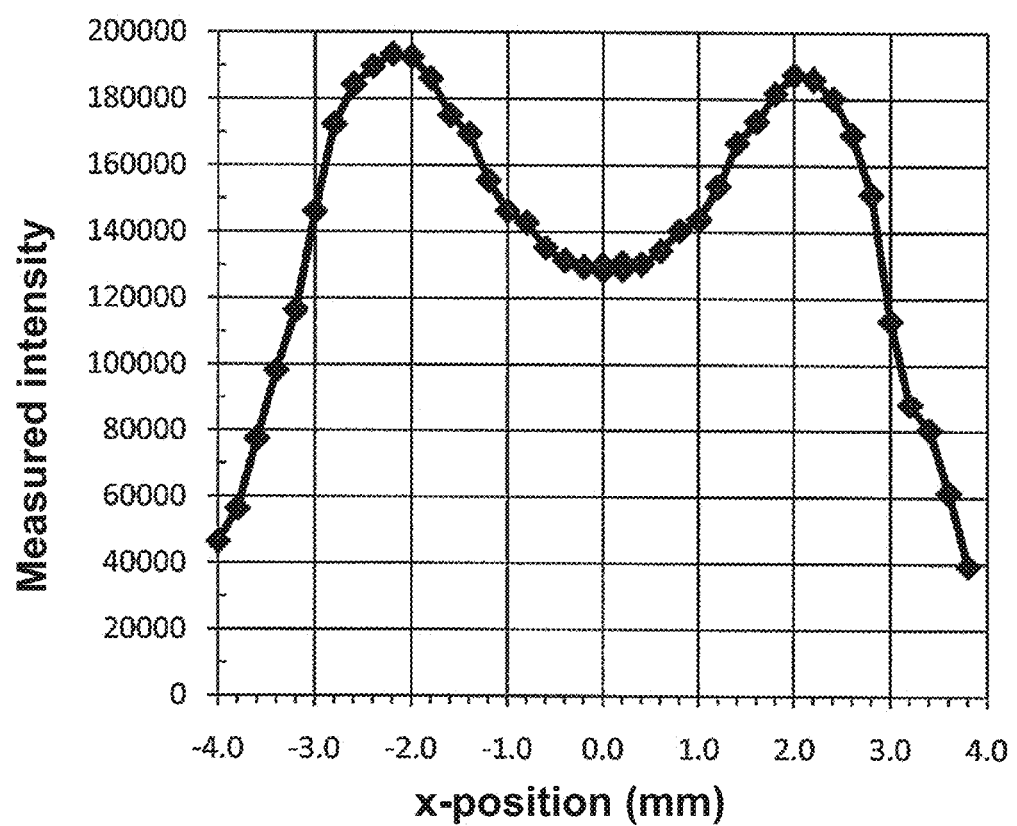
FIG. 4 shows results of optical measurements which illustrate the usability of an embodiment of the invention.

The usability of the above-described embodiment of the invention is illustrated in FIG. 4 which shows results of optical measurements where the capture range of each optical measurement is substantially an ellipsoid that is about 2.8 mm long and about 1 mm wide. The secondary axis, i.e. the 1 mm axis, of the capture range of each optical measurement substantially co-insides with a line that co-insides a diameter line of the sample well. Each black square on the curve shown in FIG. 4 represents a result of one of the optical measurements. The x-position is substantially the distance from the center point of the capture range of an optical measurement to the center of the sample well. The diameter of the sample well is about 6.7 mm. The sample well contains a dark piece of sample carrier that is situated on the middle of the bottom of the sample well. The piece is a circular disc having the diameter about 3.2 mm. The measurement solution is reference solution that is typically used for calibrating purposes. As can be seen from FIG. 4, the piece of the sample carrier attenuates the radiation measured from the middle, i.e. x≈0, of the sample well about 30-35%. Considerably less attenuated radiation can be measured from the fringes of the sample well. In these considerations, the unit of the measured intensity is immaterial. Table 1 illustrates results obtained so that only one optical measurement is taken from each sample well. Different rows of Table 1 correspond to different locations of the piece of sample carrier on the bottom of the sample well under consideration. The capture range of each optical measurement is substantially an ellipsoid that is about 2.8 mm long and about 1 mm wide, and the middle point of the capture range is substantially on the middle of the sample well. The expressions "left", "right", "up", "down", "left-up", "right-up", "left-down", and "right-down" in Table 1 illustrate the location of the piece in the sample well at each case. These expressions are to be understood with the aid of the co-ordinate system shown in FIGS. 1c-1e. For example, "right" relates to the positive x-direction and means that the piece touches the wall of the sample well in the positive x-direction. Correspondingly, "left" relates to the negative x-direction, "up" relates to the positive y-direction, "down" relates to the negative y-direction, and e.g. "right-up" means the direction of the line y=x when x increases and e.g. "left-up" means the direction of the line y=−x when x decreases. The secondary axis, i.e. the 1 mm axis, of the capture range is substantially parallel to the x-axis.

TABLE 1

| Location of the piece of sample carrier on the bottom of the sample well | Result of an optical measurement taken from the middle of the sample well |
| --- | --- |
| left | 135096 |
| right | 147787 |
| up | 121169 |
| down | 147607 |
| left-up | 121963 |
| right-up | 121425 |
| left-down | 147733 |
| right-down | 145863 |
| middle | 122925 |
| Average: | 134619 |
| Standard deviation | 9.4% |

For comparison, a corresponding result when there is no piece in the sample well is 193087. Therefore, it can be seen from Table 1 that the piece disturbs the optical measurement taken from the middle of the sample well regardless of the location of the piece.

Table 2 illustrates results obtained so that three optical measurements are taken from the sample, and the greatest one of the results is selected to be the final result. One measurement location is situated substantially in the middle of the well and the two others are situated on opposite fringes of sample well, in this case 2.2 mm away from the middle of the sample well. The secondary axis, i.e. the shorter axis, of the ellipsoid capture range of each optical measurement substantially co-insides with a line that co-insides a diameter line of the sample well.

TABLE 2

| Location of the piece of sample carrier on the bottom of the sample well | Maximum of two optical measurements taken from opposite fringes of the sample well |
| --- | --- |
| left | 188149 |
| right | 193639 |
| up | 182846 |
| down | 191814 |
| left-up | 189261 |
| right-up | 180368 |
| left-down | 195170 |
| right-down | 193036 |
| middle | 183423 |
| Average: | 188634 |
| Standard deviation | 2.8% |

The results shown in Table 2 are significantly closer to the result 193087 of the "no-piece" case than the results shown in Table 1, and the standard deviation of the results shown in Table 2 is significantly smaller than that of the results shown in Table 1.

In an optical measurement instrument according to an exemplifying embodiment of the invention, the control system 111 is configured to control the mutual positions of the sample well 153 and the measurement head 112 so that at least two of the measurement locations are situated around a z-directional straight line that goes perpendicularly through a center point of the bottom of the sample well. The distances of these at least two measurement locations from the straight line can be, for example, on the range 0.02-0.5× d, where d is the internal diameter of the opening of the sample well. One of the measurement locations can be situated substantially on the straight line, i.e. on the middle of the sample well. A case of the kind described above is illustrated in FIG. 1d, where the circles 163, 164, 165, 166 and 167 drawn with dashed lines represent the capture ranges of the optical measurements and the piece of the sample carrier is depicted with a gray circle.

The control system 111 may comprise one or more processor units each of which can be, independently of other processor units, a programmable processor unit, an application specific hardware unit, or a configurable hardware unit, e.g. a field programmable gate-array "FPGA".

Figure 2:
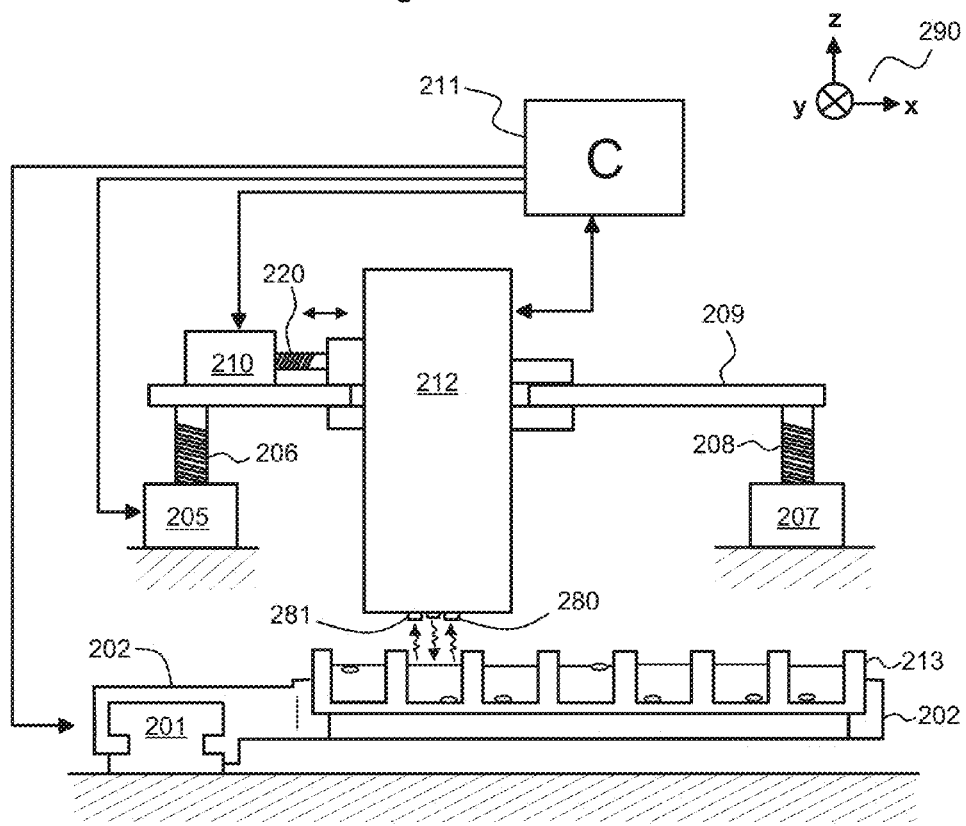
FIG. 2 shows a schematic illustration of an optical measurement instrument according to another embodiment of the invention.

FIG. 2 shows a schematic illustration of an optical measurement instrument. The optical measurement instrument comprises first mechanical support elements 201 and 202 arranged to support a sample plate 213 that can be e.g. a microtitration plate. In the exemplifying situation shown in FIG. 2, each of the sample wells of the sample plate contains measurement solution and a piece of sample carrier from which at least part of sample material has eluted in the measurement solution. The optical measurement instrument comprises second mechanical support elements arranged to support a measurement head 212 that comprises optical input interfaces 280 and 281. In the exemplifying case illustrated in FIG. 2, the second mechanical support elements comprise threaded rods 206 and 208, counterparts 205 and 207 of the threaded rods, and a planar element 209 having an aperture for the measurement head 212. The counterparts 205 and 207 of the threaded rods may comprise, for example, servomotors arranged to move the measurement head 212 in the positive or negative z-direction of the co-ordinate system 290. Furthermore, the second mechanical support elements comprise a threaded rod 220 and a counterpart 210 of the threaded rod. The counterpart 210 of the threaded rod 220 may comprise, for example, a servomotor arranged to move the measurement head 212 in the positive or negative x-direction of the co-ordinate system 290. The second mechanical support elements may further comprise a corresponding arrangement for moving the measurement head 212 in the positive or negative y-direction of the co-ordinate system 290. The optical measurement instrument comprises a control system 211 for controlling the operation of the measurement head 212. The control system is configured to control the measurement head and the second mechanical support elements so that at least two optical measurements are taken from at least two different measurement locations inside a sample well under consideration. The control system 211 can be further configured to control the second mechanical support elements to move the measurement head 212 in the positive or negative x-direction, or in the xy-plane, relative to the body of the optical measurement instrument in order to change from one of the measurement locations to another of the measurement locations, where each measurement location is a center point of a capture range from which radiation is captured in the respective optical measurement. The control system 211 is configured to form the final measurement result from the results of the at least two optical measurements in accordance with a pre-determined rule. The final measurement result can be, for example, the maximum or the arithmetic mean of the results of the at least two optical measurements.

Figure 3:
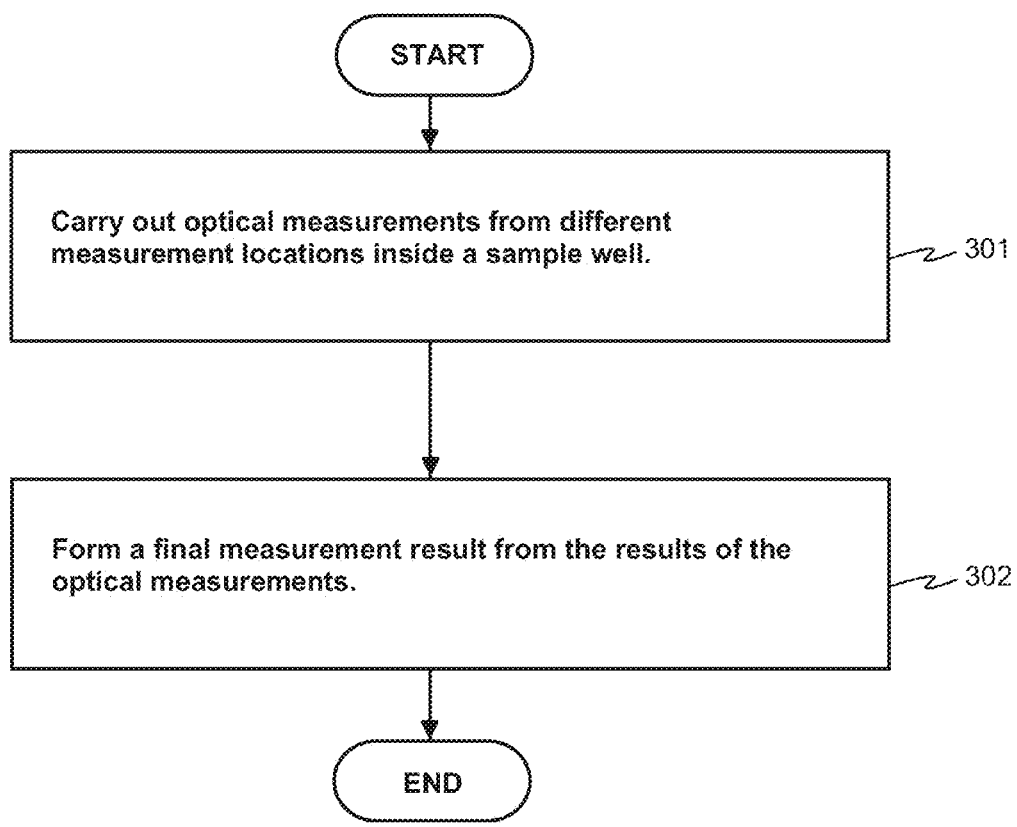
FIG. 3 shows a flow chart of a method according to an embodiment of the invention for reducing measurement variation related to optical measuring of sample material.

FIG. 3 shows a flow chart of a method according to an exemplifying embodiment of the invention for reducing measurement variation related to optical measuring of sample material. The method comprises:
  in phase 301: carrying out at least two optical measurements from at least two different measurement locations inside a sample well that contains measurement solution and a piece of sample carrier from which at least part of the sample material has eluted in the measurement solution, each measurement location being a center point of a capture range from which radiation is captured in the respective optical measurement, and subsequently
  in phase 301: forming a final measurement result from results of the at least two optical measurements in accordance with a pre-determined rule.

The use of the two or more optical measurements from the different measurement locations reduces the disturbing effect of the stochastic location of the piece of the sample carrier in the sample well. The optical measurements can be, for example, fluorescence measurements, time gated fluorescence intensity measurements, fluorescence life-time measurements, luminescence measurements, or absorbance measurements. The sample material can be, for example, blood.

It should be noted that the desired chemical reaction can also occur directly on the surface of the sample carrier, and thus the elution of the sample material is not necessary. In this case, at least one optical measurement has to be taken directly from the piece of the sample carrier. The use of at least two optical measurements from different measurement locations increases to probability that at least one optical measurement is directed to the piece of the sample carrier.

A method according to an exemplifying embodiment of the invention comprises selecting the maximum or the minimum from among the results of the at least two optical measurements, the maximum or the minimum being the final measurement result.

A method according to an exemplifying embodiment of the invention comprises calculating a weighted or non-weighted average of the results of at least two of the optical measurements, the weighted or non-weighted average being the final measurement result. In practice, when using 96-well microtitration plates having 6-7 mm well diameter, it has turned out to be appropriate that optical measurements are taken from five measurement locations inside the sample well and the final result is a weighted or non-weighted average of two or three greatest, or smallest, of the five results of the optical measurements. If the capture range is ellipsoid, it is preferred to carry out the measurements along the direction of the secondary axis of the ellipsoids as illustrated in FIG. 1e.

Figure 1C:
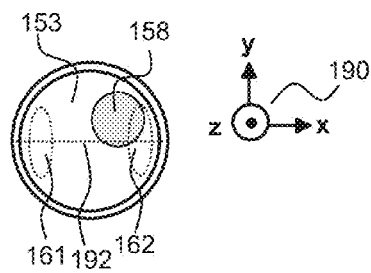
Figure 1D:
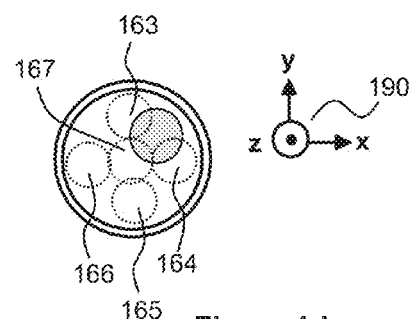
Figure 1E:
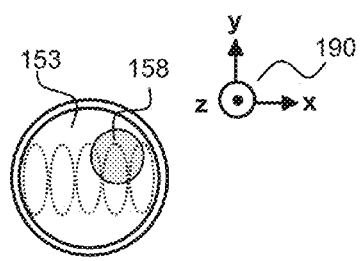

In a method according to an exemplifying embodiment of the invention, the capture range of each optical measurement is an ellipsoid and the capture ranges of two optical measurements are situated on opposite fringes of the interior of the sample well so that secondary axes of the ellipsoids representing the capture ranges of these optical measurements coincide substantially with a same diameter line of the sample well as illustrated in FIG. 1c.

In a method according to an exemplifying embodiment of the invention, at least two of the measurement locations are situated around a straight line that goes perpendicularly through the center point of the bottom of the sample well.

In a method according to an exemplifying embodiment of the invention, the distances of the above-mentioned at least two measurement locations from the above-mentioned straight line are on the range 0.02-0.5 times the internal diameter of the opening of the sample well.

In a method according to an exemplifying embodiment of the invention, one of the measurement locations is situated substantially on the above-mentioned straight line, i.e. on the middle of the sample well.

In a method according to an exemplifying embodiment of the invention, the sample well is moved when changing from one of the measurement locations to another of the measurement locations.

In a method according to an exemplifying embodiment of the invention, a measurement head is moved when changing from one of the measurement locations to another of the measurement locations.

In a method according to an exemplifying embodiment of the invention, the measurement head comprises two or more optical input interfaces suitable for capturing radiation from different measurement locations from the sample well without a need to change the mutual position of the measurement head and the sample well.

A computer program according to an exemplifying embodiment of the invention comprises software modules for the purpose of reducing measurement variation related to optical measuring of sample material. The software modules comprise computer executable instructions for controlling a programmable processor to:
  control a measurement head of an optical measurement instrument to carry out at least two optical measurements from at least two different measurement locations inside a sample well containing at least the sample material and a piece of sample carrier, each measurement location being a center point of a capture range from which radiation is captured in the respective optical measurement, and form a measurement result from results of the at least two optical measurements in accordance with a pre-determined rule.

The software modules may further comprise computer executable instructions for controlling the programmable processor to form a measurement result from results of the at least two optical measurements in accordance with a pre-determined rule.

In an exemplifying implementation of the optical measurement instrument illustrated in FIGS. 1a and 1b, the control system 111 is or includes the above-mentioned programmable processor.

The software modules can be, for example, subroutines and functions generated with a suitable programming language.

A computer program product according to an exemplifying embodiment of the invention comprises a computer readable medium, e.g. a compact disc ("CD"), encoded with the above-mentioned software modules.

A signal according to an exemplifying embodiment of the invention is encoded to carry information defining the above-mentioned software modules.

The specific examples provided in the description given above should not be construed as limiting. Therefore, the invention is not limited merely to the embodiments described above.

What is claimed is:

1. A method for reducing measurement variation related to optical measuring of sample material, comprising:
    punching or cutting off a piece from a sample carrier onto which liquid sample material has been impregnated and dried; and
    conveying the piece of the sample carrier to a sample well where at least part of the sample material elutes from the piece of the sample carrier in measurement solution contained by the sample well;
    wherein the method comprises the following steps:
    carrying out at least two optical measurements from at least two different capture ranges whose center points are inside the sample well that contains at least the sample material and the piece of the sample carrier so as to obtain at least one optical measurement whose capture range is outside the piece of the sample carrier, each capture range being a range from which radiation is captured in the respective optical measurement, the capture range of each optical measurement being an ellipse having a primary axis longer than a secondary axis and the capture ranges of two optical measurements are situated on opposite fringes of an interior of the sample well so that the secondary axes of the ellipses representing the capture ranges of these optical measurements coincide substantially with a diameter line of the sample well; and subsequently
    forming a measurement result from results of the at least two optical measurements in accordance with a pre-determined rule,
    whereby measurement variation related to optical measuring of the sample material and caused by the piece of the sample carrier contained by the sample well is reduced.

2. The method according to claim 1, wherein the center points of two or more of the capture ranges are situated around a straight line that goes through a center point of a bottom of the sample well, and is perpendicular to a bottom of the sample well.

3. The method according to claim 2, wherein the distances of the center points of the two or more of the capture ranges from the straight line are on a range 0.02-0.5 times the internal diameter of the opening of the sample well.

4. The method according to claim 2, wherein the center point of one of the capture ranges is situated substantially on the straight line.

5. The method according to claim 1, wherein the method comprises selecting the maximum or the minimum from among the results of the at least two optical measurements, the maximum or the minimum being the measurement result.

6. The method according to claim 1, wherein the method comprises calculating a weighted or non-weighted average of the results of at least two of the optical measurements, the weighted or non-weighted average being the measurement result.

7. The method according to claim 1, wherein the sample well is moved when changing from one of the capture ranges to another of the capture ranges.

8. The method according to claim 1, wherein a measurement head that receives the radiation from the sample well is moved when changing from one of the capture ranges to another of the capture ranges.

9. The method according to claim 1, wherein at least two of the optical measurements are carried out using a measurement head that comprises two or more optical input interfaces for capturing radiation from different capture ranges from the sample well without a need to change a position of the measurement head with respect to the sample well.

10. The method according to claim 1, wherein the sample material is blood.

11. The method according to claim 1, wherein the optical measurements are fluorescence measurements, time gated fluorescence intensity measurements, fluorescence life-time measurements, luminescence measurements, or absorbance measurements.

12. The method according to claim 1, wherein the method is carried out in a measurement system comprising:
    first mechanical support elements for supporting the sample well;
    second mechanical support elements for supporting a measurement head that is suitable for optical measurements;
    a measurement head attached to the second mechanical support elements;
    the sample well that contains at least sample material to be measured and a piece of sample carrier; and
    a control system for controlling operation of the measurement head.

13. The method according to claim 12, wherein the control system is configured to control the mutual position of the sample well and the measurement head so that center points of two or more of the capture ranges are situated around a straight line that goes through a center point of a bottom of the sample well, and is perpendicular to a bottom of the sample well.

14. The method according to claim 1, wherein a xenon lamp generates excitation light for the at least two optical measurements.

15. The method according to claim 1, wherein measured intensity of the at least two optical measurements peaks at ±2.0 mm along the diameter line of the sample well from a center point of the sample well.

* * * * *